United States Patent
Liu et al.

(10) Patent No.: US 12,246,308 B2
(45) Date of Patent: Mar. 11, 2025

(54) CATALYST INCLUDING MOLECULAR SIEVE HAVING TOPOLOGICAL PORE STRUCTURE, PREPARATION METHOD THEREFOR AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Chang Liu, Shanghai (CN); Yangdong Wang, Shanghai (CN); Zaiku Xie, Shanghai (CN); Su Liu, Shanghai (CN); Haibo Zhou, Shanghai (CN); Junjie Su, Shanghai (CN); Wenqian Jiao, Shanghai (CN); Lin Zhang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 135 days.

(21) Appl. No.: 18/249,718

(22) PCT Filed: Oct. 19, 2021

(86) PCT No.: PCT/CN2021/124556
§ 371 (c)(1),
(2) Date: Apr. 19, 2023

(87) PCT Pub. No.: WO2022/083564
PCT Pub. Date: Apr. 28, 2022

(65) Prior Publication Data
US 2023/0405563 A1    Dec. 21, 2023

(30) Foreign Application Priority Data
Oct. 20, 2020 (CN) .......................... 202011126552.9

(51) Int. Cl.
*B01J 29/48* (2006.01)
*B01J 23/26* (2006.01)
(Continued)

(52) U.S. Cl.
CPC ............... *B01J 29/48* (2013.01); *B01J 23/26* (2013.01); *B01J 23/34* (2013.01); *B01J 35/40* (2024.01);
(Continued)

(58) Field of Classification Search
None
See application file for complete search history.

(56) References Cited

U.S. PATENT DOCUMENTS 5,378,352 A * 1/1995 Degnan ................ B01J 29/7676
208/217
5,391,288 A * 2/1995 Collins .................. C10G 69/08
208/89

(Continued)

FOREIGN PATENT DOCUMENTS

CN    102372283 A    3/2012
CN    102039171 B    8/2012

(Continued)

OTHER PUBLICATIONS

Chang, Clarence D. et al.; "Synthesis Gas Conversion to Aromatic Hydrocarbons"; Journal of Catalysis, vol. 56, No. 2; Year: 1979; pp. 268-273.

(Continued)

*Primary Examiner* — Tam M Nguyen
(74) *Attorney, Agent, or Firm* — NKL Law; Allen Xue

(57) ABSTRACT

A catalyst contains a metal oxide, and a molecular sieve, in a crystal form, having a topological pore structure. The metal oxide is centrally distributed on the surface of the molecular sieve. Grains of the molecular sieve are exposed to at least three families of crystal planes. The family of crystal plane with the largest pore size in topology is occupied by the metal oxide by no more than 30%, preferably no more than 20%, or no more than 10%.

17 Claims, 3 Drawing Sheets

(51) Int. Cl.

| | | |
|---|---|---|
| *B01J 23/34* | (2006.01) | |
| *B01J 35/40* | (2024.01) | |
| *B01J 37/08* | (2006.01) | |
| *C01B 39/02* | (2006.01) | |
| *C01B 39/36* | (2006.01) | |
| *C01B 39/40* | (2006.01) | |
| *C07C 1/04* | (2006.01) | |

(52) U.S. Cl.
CPC ........... *B01J 37/082* (2013.01); *C01B 39/026* (2013.01); *C01B 39/365* (2013.01); *C01B 39/40* (2013.01); *C07C 1/043* (2013.01); *C07C 1/0445* (2013.01); *B01J 2229/186* (2013.01); *C01P 2002/72* (2013.01); *C01P 2004/03* (2013.01); *C07C 2529/40* (2013.01)

(56) References Cited

U.S. PATENT DOCUMENTS

| | | | | |
|---|---|---|---|---|
| 2002/0164283 | A1* | 11/2002 | Jones | C01B 37/00 423/702 |
| 2012/0088944 | A1 | 4/2012 | Buijs et al. | |
| 2021/0380888 | A1* | 12/2021 | Jiao | B01J 29/703 |
| 2022/0280912 | A1* | 9/2022 | Fu | B01J 20/2808 |
| 2022/0281752 | A1* | 9/2022 | Arulraj | C01B 39/48 |

FOREIGN PATENT DOCUMENTS

| | | |
|---|---|---|
| CN | 102372277 B | 1/2013 |
| CN | 102371169 B | 4/2013 |
| CN | 102371170 B | 4/2013 |
| CN | 107469857 A | 12/2017 |
| CN | 107486234 A | 12/2017 |
| CN | 108622913 A | 10/2018 |
| CN | 106540740 B | 9/2019 |
| CN | 111111752 A | 5/2020 |

OTHER PUBLICATIONS

Erena, Javier et al.; "Study of Physical Mixtures of $Cr_2O_3$—ZnO and ZSM-5 Catalysts for the Transformation of Syngas into Liquid Hydrocarbons"; Industrial&Engineering Chemistry Research, vol. 37; Mar. 13, 1998, pp. 1211-1219.

Cheng, Kang et al.; "Bifunctional Catalysts for One-Step Conversion of Syngas into Aromatics with Excellent Selectivity and Stability"; Chem., vol. 3; Aug. 10, 2017; pp. 1-14.

Yang, Junhao et al.; "Direct conversion of syngas to aromatics"; Chemical Communications, vol. 53; Jun. 19, 2017; pp. 1-12.

Huang, Zhen et al.; "Ceria-Zirconia/Zeolite Bifunctional Catalyst for Highly Selective Conversion of Syngas into Aromatics"; Chem. Cat.Chem., vol. 10; Year: 2018,pp. 4519-4524.

Zhou, Wei et al.; "Selective Conversion of Syngas to Aromatics over a Mo—$ZrO_2$/H-ZSM-5 Bifunctional Catalyst"; Chem.Cat. Chem., vol. 11; Year: 2019, pp. 1-9.

* cited by examiner

CATALYST INCLUDING MOLECULAR SIEVE HAVING TOPOLOGICAL PORE STRUCTURE, PREPARATION METHOD THEREFOR AND USE THEREOF

TECHNICAL FIELD

The invention relates to a catalyst for producing aromatic hydrocarbons and/or light hydrocarbons by conversion of synthesis gas, a preparation process and application thereof.

BACKGROUND

Light aromatic hydrocarbons are important basic chemicals and have been widely used for the production of synthetic resins, rayon, synthetic rubbers, and the like. Under the current situation that petroleum resources are increasingly reduced, the technology for producing aromatic hydrocarbons by a novel non-petroleum-based route has been researched and developed. There are two main routes for preparing the aromatic compound by taking the synthesis gas as a raw material, namely the route based on alcohol synthesis and the route based on Fischer-Tropsch synthesis. The route based on alcohol synthesis is an indirect route, and the existing mature process can be used for reference, but the production route is longer and the equipment investment is higher; while the product distribution of the Fischer-Tropsch synthesis is wide and is limited by the Anderson-Schulz-Flory distribution, and the selectivity to aromatic hydrocarbon product is low.

A one-step process based on the CO hydrogenation-intermediate conversion multifunctional catalyst has the advantages of low fixed cost demand, providing possibility for realizing high-efficiency coupling among multiple steps of reactions and promoting the shift of reaction equilibrium, therefore shows both the academic and application values. C. D. Chang et al (Synthesis gas conversion to aromatic hydrocarbons. Journal of Catalysis, 1979, 56(2): 268-273) applied $ZnO-Cr_2O_3$ and HZSM-5 in the production of aromatic hydrocarbons from synthesis gas, resulting in a total selectivity of nearly 70% to aromatic hydrocarbons. E. Javier et al (Industrial & Engineering Chemistry Research, 1998, 37, 1211-1219) mechanically mixed $Cr_2O_3$—ZnO with a HZSM-5 molecular sieve with Si/Al=154, resulting in direct preparation of gasoline from synthesis gas through the methanol intermediate. Zn—Zr oxide, Zn—Cr oxide, Ce—Zr oxide and Mo—Zr oxide are respectively coupled with ZSM-5 molecular sieves by K. Cheng et al (Chem, 2017, 3, 1-14), J. Yang et al (Chemical Communications, 2017, 53, 11146-11149), Z. Huang et al (Chem Cat Chem, 2018, 10, 4519-4524) and W. Zhou et al (Chem Cat Chem, 2019, 11, 1-9), thereby realizing the conversion of synthesis gas to aromatic hydrocarbon. CN 201610965244.2 and CN 201710603524.3 disclose applications of zirconium-containing composite oxide-modified zeolite molecular sieve, modified cerium-zirconium solid solution-hierarchical aluminium silicate solid acid material in preparation of light aromatic hydrocarbon by conversion of synthesis gas, respectively. Generally, the multifunctional catalyst can achieve higher selectivity to aromatic hydrocarbons, but the conversion is still low, and the regulation of the aromatic distribution on the basis of maintaining high yield of the aromatic hydrocarbon is still difficult.

When a molecular sieve is used as one of the active components to prepare a shaped catalyst, a large amount of binder is usually added to improve the mechanical strength of the catalyst to meet the requirements of industrial production. However, the addition of the binder in turn leads to a decrease in the proportion of active components and thus to a decrease in the activity of the catalyst. For this reason, researchers have conducted a recrystallization treatment on the binder in the shaped catalyst, so as to reduce the components of the binder and simultaneously enable the catalyst to have higher mechanical strength (such as CN102371169B, CN102371170B, CN102039171B and CN 102372277B).

At present, multifunctional shaped catalysts for producing aromatic hydrocarbons and/or light hydrocarbons by converting synthesis gas have been developed, which contain metal oxides and molecular sieves, but the development of multifunctional catalysts is still in the research stage, and the coupling performance is still required to be improved.

SUMMARY OF THE INVENTION

The invention provides a catalyst comprising a molecular sieve having a topological pore structure, a preparation process thereof and use of the catalyst in a process for producing aromatic hydrocarbons and/or light hydrocarbons by conversion of synthesis gas. When the catalyst is used for producing aromatic hydrocarbons and/or light hydrocarbons by conversion of synthesis gas, the activity of the catalyst is obviously improved, and the selectivity and distribution of the aromatic hydrocarbons are better.

All publications, patent applications, patents, and other references mentioned in this specification are herein incorporated by reference in their entirety. Unless defined specifically, all technical and scientific terms used herein have the same meaning as commonly understood by those skilled in the art to which this invention belongs. In case of conflict, the present specification, including definitions, will control.

All ranges involved herein are inclusive of their endpoints unless specifically stated otherwise. Further, when a range, one or more preferred ranges, or a plurality of preferable upper and lower limits, are given for an amount, concentration, or other value or parameter, it is to be understood that all ranges formed from any pair of any upper limit or preferred values thereof and any lower limit or preferred values thereof are specifically disclosed, regardless of whether such pairs of values are individually disclosed.

In the present invention, when a technical solution is given in an open-ended limited form such as "including", "including" some listed elements, it will be understood by those skilled in the art that an embodiment consisting of, or consisting essentially of, these elements can be obviously used to implement the technical solution. Therefore, those skilled in the art will understand that the technical solution given in the present invention with the open limitation also covers the embodiments constituted by the enumerated elements, or substantially constituted by the enumerated elements.

Finally, all percentages, parts, ratios, etc. referred to in this specification are by weight unless explicitly stated otherwise; but where weight is not a basis according to conventional wisdom by those skilled in the art, the basis is determined by conventional wisdom by those skilled in the art.

"Ranges" as disclosed herein are given with lower and upper limits, e.g., one or more lower limits and one or more upper limits. A given range may be defined by selecting a lower limit and an upper limit that define the boundaries of the given range. All ranges defined in this manner are inclusive and combinable, i.e., any lower limit may be combined with any upper limit to form a range. For example, ranges of 60-110 and 80-120 are listed for particular parameters, meaning that ranges of 60-120 and 80-110 are also contemplated. Furthermore, if the lower limits listed are 1 and 2 and the upper limits listed are 3, 4 and 5, then the following ranges are all contemplated: 1-3, 1-4, 1-5, 2-3, 2-4, and 2-5.

For the purposes of the present invention, a catalyst is understood to mean a catalyst having regular shape, a certain particle size and strength, comprising two components of both a metal oxide and a molecular sieve.

For the purposes of the present invention, the distance from the metal oxide to the surface of the molecular sieve crystal grain refers to the perpendicular distance from the center of the metal oxide particle to the outer surface of the molecular sieve crystal grain.

One aspect of the present invention provides a catalyst comprising a molecular sieve having a topological pore structure, the catalyst comprising a metal oxide and the molecular sieve having a topological pore structure in a crystal form, the metal oxide being concentrated on the surface of the molecular sieve; wherein the crystal grains of the molecular sieve expose at least 3 families of crystal planes, among which the 1 family with the relatively largest channel size in topology is occupied by the metal oxide by no more than 30%, preferably no more than 20%, or no more than 10%.

In an exemplary embodiment, at least 70%, preferably at least 80%, or at least 90%, of the metal oxide is distributed on the 2 families of crystal planes with the topologically relatively smallest channel size. In an exemplary embodiment, accounting the weight of metal oxide distributed per area on the crystal plane with the topologically largest channel size as 1, then the weight of metal oxide distributed per area on the crystal plane with the topologically smallest channel size is greater than 2, preferably greater than 3; in other words, in terms of the weight of the metal oxide distributed per unit area on the crystal plane (may be briefly called as weight per unit area), the weight of the metal oxide per unit area on the crystal plane having the topologically smallest channel size exceeds by 2 times, preferably by 3 times, of the weight of the metal oxide per unit area on the crystal plane having the topologically largest channel size.

For the purposes of the present invention, the metal oxide is "concentrated" on the surface of the molecular sieve, meaning that a major portion of the metal oxide is distributed on the surface of the molecular sieve; for example, in one exemplary embodiment, at least 50% of the metal oxide is distributed on the surface of the molecular sieve, preferably at least 70% is distributed on the surface of the molecular sieve. In one exemplary embodiment, the present invention thus provides a catalyst comprising a metal oxide and a molecular sieve, the metal oxide being distributed substantially all on the surface of the molecular sieve.

In an exemplary embodiment, at most 30% of the metal oxide is distributed in a range having a distance of more than 200 nm from the surface of the molecular sieve crystal grains; preferably at most 25% is distributed in a range having a distance of more than 100 nm from the surface of the molecular sieve crystal grains.

In one embodiment, the molecular sieve is selected from the group consisting of MFI, MEL, AEL, TON, and other molecular sieves having a ten-member ring structure. Preferably, the molecular sieve is selected from MFI and MEL structural molecular sieves. Further preferably, the molecular sieve is selected from ZSM-5, ZSM-11, Silicalite-1 and Silicalite-2. More preferably, the molecular sieve is selected from ZSM-5 and ZSM-11.

In one embodiment, the molecular sieve has a silica-alumina molar ratio of 15-∞, preferably 15-200, and more preferably 20-100.

In one embodiment, the molecular sieve has a grain size of 10 nm-2000 nm, preferably 50 nm-800 nm, and more preferably 400-800 nm.

In one embodiment, preferably, the molecular sieve is a ZSM-5 molecular sieve. The metal oxide is mainly distributed on a crystal plane (100) and a crystal plane (101) of the ZSM-5 molecular sieve. The crystal planes of the ZSM-5 molecular sieve mainly comprise a crystal plane (100), a crystal plane (101) and a crystal plane (010), where the metal oxide is mainly distributed on the crystal plane (100) and the crystal plane (101) of the ZSM-5 molecular sieve (accounting for more than 70% of the total amount of the metal oxide), and is obviously less distributed on the crystal plane (010).

In one embodiment, preferably, the molecular sieve is a ZSM-11 molecular sieve. The metal oxide is mainly distributed on the crystal plane (101) of the ZSM-11 molecular sieve. The metal oxide is mainly distributed on the crystal plane (101) of the ZSM-11 molecular sieve (accounting for more than 50% of the total amount of the metal oxide), and is obviously less distributed on other crystal planes such as (100), (010) and, if any, others.

In one embodiment, the catalyst comprises up to 5 wt % of amorphous silica and/or amorphous alumina phases, preferably up to 3 wt % of amorphous silica and/or amorphous alumina phases, preferably up to 1 wt % of amorphous silica and/or amorphous alumina phases, relative to the total weight of the catalyst. Preferably, the catalyst is free of amorphous silica and/or amorphous alumina phases, relative to the total weight of the catalyst.

Accordingly, in one embodiment, the XRD spectrum of the catalyst is substantially free of characteristic diffraction peaks of amorphous silica and/or amorphous alumina. For the purposes of the present invention, the phrase "substantially free of . . . characteristic diffraction peaks" means that there are no characteristic diffraction peaks at the relevant location sufficient to be identified in the art as being representative of the presence of the corresponding structure. The silica or alumina is a binder conventionally used in the art; thus, in other words, the catalyst of the invention is substantially free of the amorphous binder component. Accordingly, such a catalyst of the invention substantially free of amorphous binder and having a regular shape, certain particle size and strength can be referred to as an "integral" catalyst.

In one embodiment, the precursor of the amorphous silica and/or amorphous alumina phase in the catalyst is a binder.

In one embodiment, the weight ratio of the metal oxide to the molecular sieve in the catalyst is (0.2-5.0): 1, preferably (0.4-2.5): 1.

In one embodiment, preferably, the metal component of the metal oxide is selected from the group consisting of rare earth metals, Group IVB, Group VIB, Group VIIB, Group VIII, Group IB, Group IIB, and Group IIIA elements.

In one embodiment, more preferably, the metal component of the metal oxide is selected from Cr, Zr, Mn, Ce, La, In, Ga and Zn.

In one embodiment, more preferably, the metal component of the metal oxide is selected from Cr, Zr, Mn, In and Zn.

In one embodiment, more preferably, the metal component of the metal oxide is selected from Zn, Ce, Ga and La.

More preferably, in one embodiment, the metal oxide is selected from $Cr_2O_3$, $MnO$, $ZnMn_{20}O_x$ and $CrMnO_x$.

In one embodiment, the catalyst particles have a particle size of from 0.1 mm to 10.0 mm, preferably from 1.0 to 5.0 mm.

In another aspect, the present invention provides a process for preparing the catalyst of the present invention, comprising: mixing and shaping the metal oxide, the molecular sieve in the prepared form and the binder, carrying out a second crystallization treatment in a second template agent vapor atmosphere, and calcining to obtain the catalyst. Preferably, in this process, the molecular sieve in the prepared form is prepared with the aid of a first templating agent that is the same as or different from the second templating agent and is not calcined.

Thus, in one embodiment, the molecular sieve is a molecular sieve in the prepared form, i.e., a molecular sieve obtained without calcination of the crystallized product. The preparation process of the molecular sieve comprises the step of adding an ammonium based adjuvant in the process of preparing the crystallization mother liquor. In the invention, by adding an ammonium based adjuvant which is a substance capable of providing ammonium ions in the process of synthesizing the molecular sieve, the adjuvant can be selectively adsorbed on a specific crystal plane of the molecular sieve through the ammonium ions, so that the metal oxide introduced in the subsequent preparation of the catalyst is selectively adsorbed on other specific crystal planes except the specific crystal plane above, for example, for ZSM-5, the metal oxide is selectively adsorbed on a crystal plane (100) and a crystal plane (101). Through the inventors' study, the activity of the catalyst can be greatly improved to improve the conversion rate of CO in the synthesis gas.

In one embodiment, the ammonium based adjuvant is ammonia, urea, ammonium carbonate, or ammonium bicarbonate. The molar ratio of the ammonium based adjuvant to the silicon source calculated as $SiO_2$ in the molecular sieve is 0.2-5.0, preferably 0.5-3.0, such as 0.5-2.0.

In one embodiment, taking a ZSM-5 molecular sieve as an example, the molecular sieve is prepared by a process comprising: mixing a silicon source, an aluminum source, a first template agent, an ammonium based adjuvant and an optionally added alkali source to obtain a crystallization mother liquor, and drying after first crystallization to obtain the molecular sieve in the prepared form. The silicon source is selected from silica sol, fumed silica, ethyl orthosilicate and sodium silicate, wherein the aluminum source is selected from aluminum isopropoxide, aluminum nitrate, aluminum hydroxide, aluminum sol and sodium metaaluminate, the alkali source is selected from sodium hydroxide, sodium carbonate and sodium bicarbonate, the template agent is selected from tetrapropyl ammonium bromide and tetrapropyl ammonium hydroxide, and the ammonium based adjuvant is ammonia, urea, ammonium carbonate or ammonium bicarbonate. The molar ratio of the silicon source calculated as $SiO_2$, the aluminum source calculated as $Al_2O_3$, the alkali source calculated as oxide, the template agent and the ammonium based adjuvant is 1: 0-0.033:0-2.0:0.2-4.0:0.2-5.0. The crystallization is carried out under conditions comprising: a crystallization temperature of 120-200° C., and a crystallization duration of 12-180 hours. The ZSM-5 molecular sieve obtained has a particle size of 10 nm-2000 nm, preferably 50 nm-800 nm, and more preferably 400-800 nm.

In one embodiment, taking a ZSM-11 molecular sieve as an example, the molecular sieve is prepared by a process comprising: mixing a silicon source, an aluminum source, a first template agent, an ammonium based adjuvant and an optionally added alkali source to obtain a crystallization mother liquor, and drying after first crystallization to obtain the synthetic molecular sieve. The silicon source is selected from silica sol, fumed silica, ethyl orthosilicate and sodium silicate, the aluminum source is selected from aluminum isopropoxide, aluminum nitrate, aluminum hydroxide, aluminum sol and sodium metaaluminate, the alkali source is selected from sodium hydroxide, sodium carbonate and sodium bicarbonate, the template agent is selected from tetrabutylammonium bromide and tetrabutylammonium hydroxide, and the ammonium based adjuvant is ammonia, urea, ammonium carbonate or ammonium bicarbonate. The molar ratio of the silicon source calculated as $SiO_2$, the aluminum source calculated as $A_2O_3$, the alkali source calculated as an oxide, the template agent and the ammonium based adjuvant is 1: 0-0.033:0-2.0:0.2-4.0:0.2-5.0. The crystallization is carried out under conditions comprising: a crystallization temperature of 120-200° C., and a crystallization duration of 12-180 hours. The ZSM-11 molecular sieve obtained has a particle size of 10 nm-2000 nm, preferably 50 nm-800 nm, and more preferably 400-800 nm.

In one embodiment, the second templating agent is selected from the group consisting of aqueous ammonia, triethylamine, tetraethylammonium bromide, tetraethylammonium hydroxide, tetrapropylammonium bromide, tetrapropylammonium hydroxide, tetrabutylammonium bromide, and tetrabutylammonium hydroxide.

In one embodiment, the second crystallization is carried out under conditions comprising: a crystallization temperature of 100-180° C.; and a crystallization duration of 12-100 hours, preferably, a crystallization temperature of 105-170° C.; and a crystallization duration of 24-96 hours.

In one embodiment, the calcination is carried out under conditions comprising: a calcining temperature of 500-700° C., and a calcining duration of 2-10 hours; preferably, a calcining temperature of 520-580° C., and a calcining duration of 5-8 hours.

In one embodiment, preferably, the binder is selected from the group consisting of silica sol, fumed silica, aluminum nitrate, aluminum hydroxide, aluminum sol, silica alumina sol, and the molecular sieve mother liquor.

In one embodiment, the weight ratio of the metal oxide/molecular sieve/binder is preferably in the range of (0.2-5.0): 1:(0.2-0.6).

In one embodiment, more preferably, the weight ratio of metal oxide/molecular sieve/binder is in the range of (0.4-2.5): 1:(0.3-0.5).

The invention further provides a process for producing aromatic hydrocarbons and/or light hydrocarbons by conversion of synthesis gas, using the synthesis gas as a raw material, which raw material is contacted and reacted with the catalyst according to the present invention to obtain a stream comprising the aromatic hydrocarbons and/or the light hydrocarbons.

In one embodiment, preferably, the raw material of the synthesis gas has a $H_2/CO$ molar ratio in the range of 0.3 to 4.0.

In one embodiment, further preferably, the raw material of the synthesis gas has a $H_2/CO$ molar ratio in the range of 0.5 to 2.0.

In one embodiment, preferably, the reaction is carried out under conditions comprising: a reaction temperature of 350-480° C.; and/or a reaction pressure of 2.0-9.5 MPa; and/or a volume space velocity of 900-18000 $h^{-1}$.

In one embodiment, more preferably, the reaction is carried out under conditions comprising: a reaction temperature of 350-450° C.; and/or a reaction pressure of 4.0-8.0 MPa; and/or a volume space velocity of 1000-15000 $h^{-1}$.

The present invention provides a novel process for the preparation of aromatics and/or lighter hydrocarbons from synthesis gas, the products of which comprise BTX aromatics, $C_{9+}$ aromatics, and/or $C_1$-$C_{5+}$ light hydrocarbons. One-stage reactor or multi-stage reactors in series can be used, and the reactor can be fixed bed, fluidized bed or moving bed. For a system of multi-stage reactors in series, the reactors may be the same or different. The $H_2$/CO molar ratio of the synthesis gas from different sources can be adjusted by using water gas shift treatment/reverse water gas shift treatment. The $H_2O$ and $CO_2$ required for the treatment was partly derived from separation and reflux of the reaction product and partly from a pipeline feed gas.

In the invention, the reacted stream comprises unconverted CO and $H_2$, $CO_2$ and hydrocarbon products, wherein the hydrocarbon products comprise aromatic hydrocarbons and/or $C_1$-$C_{5+}$ hydrocarbons. The aromatic hydrocarbons comprises $C_6$-$C_{9+}$ aromatic hydrocarbons, and $C_{5+}$ hydrocarbons refer to aliphatic hydrocarbon compounds having more than 5 carbon atoms. The selectivity to each product is defined as the ratio (mol %) of the each product to the total organic products, based on carbon number. The specific calculation methods are as follows:

Total carbon number of organic products=Σ(moles of organic product *i*×number of carbon atoms in the molecule of the organic product *i*)

Selectivity to organic product *j*=moles of organic product *j*×number of carbon atoms in the molecule of the organic product *j*/total carbon number of organic products×100%

Selectivity to aromatics=selectivity to $C_6$ aromatics+ selectivity to $C_7$ aromatics+selectivity to $C_8$ aromatics+selectivity to $C_{9+}$aromatics Selectivity to $C_6$-$C_8$ aromatics=(selectivity to $C_6$ aromatics+selectivity to $C_7$ aromatics+selectivity to $C_8$ aromatics)/selectivity to aromatics×100%.

Among the aromatic hydrocarbon products, benzene, toluene and xylene are widely used as chemical raw materials, solvents and gasoline additives, and with high industrial value, and an important method for improving the yield of the aromatic hydrocarbons is to improve the activity of a catalyst so as to convert more raw materials into the target products. In addition, adjustment of the distribution of aromatic hydrocarbon products and increase of the selectivity to $C_6$-$C_8$ light aromatic hydrocarbons are problems to be solved for a system of preparing aromatic hydrocarbons and/or light hydrocarbons from synthesis gas.

Using the catalyst according to the present invention, high-efficiency coupling and path regulation of a multi-step reaction are realized by selecting out preferred active components of the catalyst and adjusting the distribution state of metal oxides on the molecular sieve in the catalyst system, so that the catalytic activity is obviously improved, and the distribution of aromatic hydrocarbons is optimized accompanied with a selectivity to high aromatic hydrocarbons. When the catalyst according to the present invention is used in the reaction of preparing aromatic hydrocarbons from synthesis gas, the distribution of the aromatic hydrocarbons is excellent, the selectivity to the total aromatic hydrocarbons reaches more than 70%, and more remarkably, the conversion rate of CO can reach more than 35%.

EMBODIMENTS OF THE INVENTION

Figure 1:
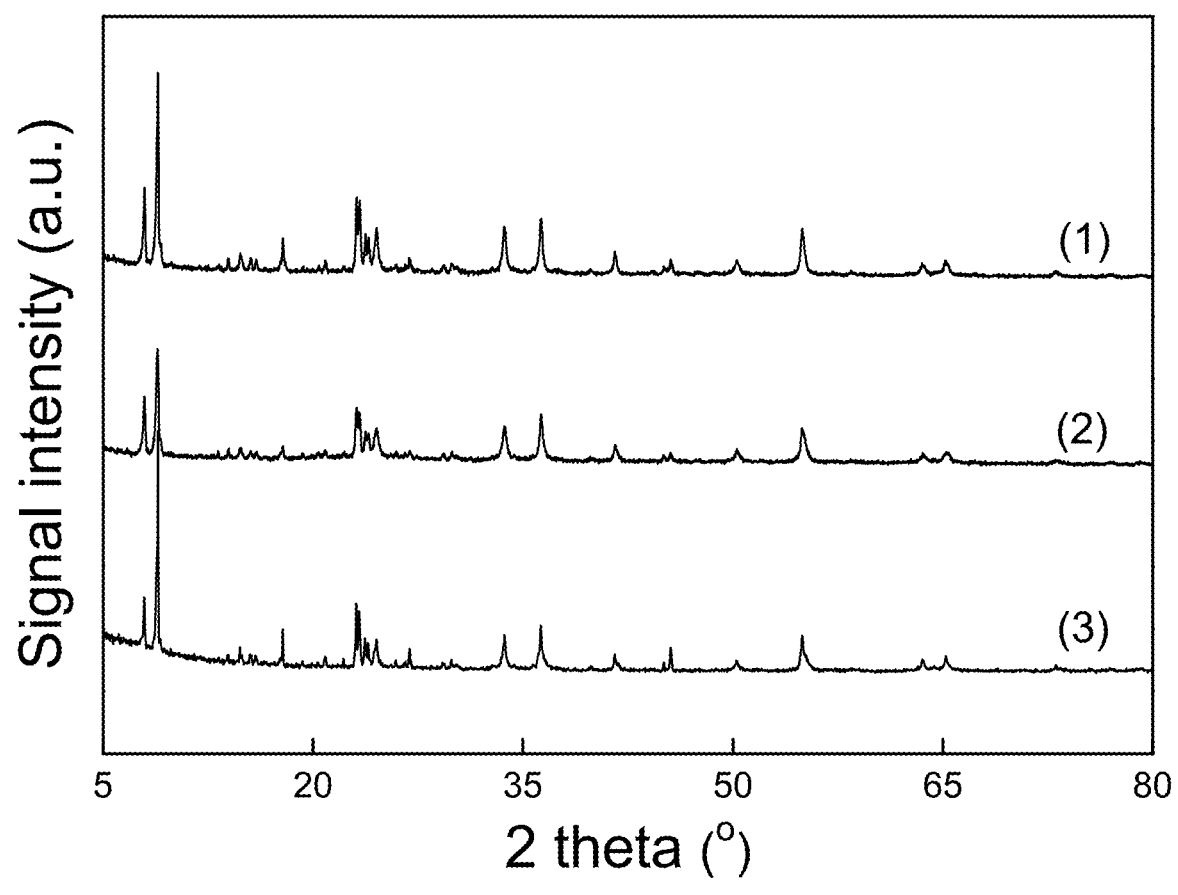
In FIG. 1, panels (1), (2) and (3) are XRD spectra of the catalysts obtained in Example 7, Comparative Example 2 and Comparative Example 1, respectively.

Reference will now be made in detail to the embodiments of the present invention, but it should be understood that the scope of the invention is not limited by the embodiments, but is defined by the appended claims.

Instrument and conditions for the XRD test of the catalyst involved by the present invention are as follows: the phase analysis of the catalyst was carried out at room temperature using an X-ray diffractometer, model Bruker D8 Advance, using a Cu-Kα1 radiation source (λ=0.15405 nm) and a graphite monochromator at a tube pressure of 40 kV, a tube current of 50 mA and a scanning range of 5 to 90°.

Instrument and conditions for the SEM test of the catalyst involved by the present invention are as follows: the morphology and structure of the catalyst were observed with a scanning electron microscope (Zeiss Merlin) at an acceleration voltage of 2.0 kV.

According to the invention, a BL07W beamlines station "water window" soft X-ray microscopy absorption 3D microscopy imaging (Nano-CT) from National Synchrotron Radiation Laboratory, Hefei, China, was used to characterize the distribution of metal oxides on the surface of a molecular sieve.

The present invention will be described in further detail with reference to Examples.

Example A

MnO was prepared by a precipitation process: a 50% manganese nitrate solution was used as a manganese source, and ammonium carbonate was used as a precipitator. 50.11 g of manganese nitrate solution was diluted with 50 mL of deionized water to obtain a uniform solution; 19.22 g of ammonium carbonate was dissolved in 100.0 mL of deionized water. The manganese nitrate solution was added dropwise cocurrently with the ammonium carbonate solution to 20 mL of deionized water in a 70° C. thermostatic water bath with vigorous stirring. After the precipitation was finished, the mother liquor was aged in a 70° C. thermostatic waterbath for 3 h, filtered and washed with deionized water until the filtrate was neutral, and the filter cake was dried in a 100° C. oven overnight, and calcined at 500° C. (with a temperature-rising rate of 2° C./min) for 1 h to obtain MnO.

Example B

A hydrothermal process was used to synthesize a ZSM-5 molecular sieve (marked as Z5 (50)-450 nm) with a Si/Al molar ratio of 50 and an average particle size of 450 nm, comprising the steps of:

0.41 g of aluminum isopropoxide was added to a mixed solution of 24.67 g of tetrapropylammonium hydroxide solution (25 wt %) and 17.89 g of deionized water. The mixture was placed and stirred at room temperature for 12 h, then 21.06 g of ethyl orthosilicate was added dropwise. After stirring for 12 h, 10.63 g urea was added to the mixed system and stirring was continued for 1 h. The mother liquor was transferred to a PTFE lined autoclave and hydrothermally treated in a 180° C. oven for 48 h. The liquor was centrifugally separated and repeatedly washed with deionized water until the supernatant was neutral, and dried to obtain a solid product, namely an uncalcined ZSM-5 sample, wherein an XRD spectrum thereof was shown in FIG. 2.

Example C $Cr_2O_3$ was prepared by a precipitation process: chromium nitrate nonahydrate was used as a chromium source, and ammonium carbonate was used as a precipitator. 56.02 g of chromic nitrate was dissolved in 75 mL of deionized water; and 21.19 g of ammonium carbonate was dissolved in 100.0 mL of deionized water. The chromic nitrate solution was added dropwise cocurrently with the ammonium carbonate solution to 20 ml mL of deionized water in a 70° C. thermostatic waterbath with vigorous stirring. After the precipitation was finished, the mother liquor was aged in a 70° C. thermostatic waterbath for 3 h, filtered and washed with deionized water until the filtrate was neutral, and the filter cake was dried in a 100° C. oven overnight, and calcined at 500° C. (with a temperature-rising rate of 2° C./min) for 1 h to obtain $Cr_2O_3$.

Example D $CrMnO_x$ was prepared by a ball mill mixing-calcining process: chromium nitrate nonahydrate and a 50% manganous nitrate solution were respectively used as a chromium source and manganese source, and ammonium carbonate was used as a precipitator. 56.02 g of chromic nitrate was dissolved in 75 mL of deionized water; and 21.19 g of ammonium carbonate was dissolved in 100.0 mL of deionized water. The chromic nitrate solution was added dropwise cocurrently with the ammonium carbonate solution to 20 mL of deionized water in a 70° C. thermostatic waterbath with vigorous stirring. After the precipitation was finished, the mother liquor was aged in a 70° C. thermostatic waterbath for 3 h, filtered and washed with deionized water until the filtrate was neutral, and the filter cake was dried in a 100° C. oven overnight, to obtain a chromium precursor. 50.11 g of manganese nitrate solution was diluted with 50 mL of deionized water to obtain a uniform solution; 19.22 g of ammonium carbonate was dissolved in 100.0 mL of deionized water. The manganous nitrate solution was added dropwise cocurrently with the ammonium carbonate solution to 20 mL of deionized water in a 70° C. thermostatic waterbath with vigorous stirring. After the precipitation was finished, the mother liquor was aged in a 70° C. thermostatic waterbath for 3 h, filtered and washed with deionized water until neutral, and the filter cake was dried in a 100° C. oven overnight, to obtain a manganese precursor. The chromium precursor and manganese precursor were mixed by ball milling, and the mixture obtained was calcined further at 500° C. (a temperature-rising rate of 2° C./min), to obtain $CrMnO_x$.

Example E

A hydrothermal process was used to synthesize a ZSM-11 molecular sieve (marked as Z11 (50)-450 nm) with a Si/Al molar ratio of 50 and an average particle size of 450 nm, comprising the steps of:

0.41 g of aluminum isopropoxide was added to a mixed solution of 19.67 g of tetrabutylammonium hydroxide solution (40 wt %) and 17.89 g of deionized water. The mixture was placed and stirred at room temperature for 12 h, then 21.06 g of ethyl orthosilicate was added dropwise. After stirring for 12 h, 10.63 g urea was added to the mixed system and stirring was continued for 1 h. The mother liquor was transferred to a PTFE lined autoclave and hydrothermally treated in a 180° C. oven for 48 h. The liquor was centrifugally separated and repeatedly washed with deionized water until the supernatant was neutral, and dried to obtain a solid product, namely an uncalcined ZSM-11 sample.

Example F

A hydrothermal process was used to synthesize a ZSM-5 molecular sieve (marked as Z5 (50)-200 nm) with a Si/Al molar ratio of 50 and an average particle size of 200 nm, comprising the steps of:

0.41 g of aluminum isopropoxide was added to a mixed solution of 24.67 g of tetrapropylammonium hydroxide solution (25 wt %) and 17.89 g of deionized water. The mixture was placed and stirred at room temperature for 12 h, then 21.06 g of ethyl orthosilicate was added dropwise. After stirring for 12 h, 3.04 g urea was added to the mixed system and stirring was continued for 1 h. The mother liquor was transferred to a PTFE lined autoclave and hydrothermally treated in a 180° C. oven for 48 h. The liquor was centrifugally separated and repeatedly washed with deionized water until the supernatant was neutral, and dried to obtain a solid product, namely an uncalcined ZSM-5 sample, wherein an XRD spectrum thereof was shown in FIG. 2.

Example G

A hydrothermal process was used to synthesize a ZSM-5 molecular sieve (marked as Z5 (50)-300 nm) with a Si/Al molar ratio of 50 and an average particle size of 300 nm, comprising the steps of:

0.41 g of aluminum isopropoxide was added to a mixed solution of 24.67 g of tetrapropylammonium hydroxide solution (25 wt %) and 17.89 g of deionized water. The mixture was placed and stirred at room temperature for 12 h, then 21.06 g of ethyl orthosilicate was added dropwise. After stirring for 12 h, 7.59 g urea was added to the mixed system and stirring was continued for 1 h. The mother liquor was transferred to a PTFE lined autoclave and hydrothermally treated in a 180° C. oven for 48 h. The liquor was centrifugally separated and repeatedly washed with deionized water until the supernatant was neutral, and dried to obtain a solid product, namely an uncalcined ZSM-5 sample, wherein an XRD spectrum thereof was shown in FIG. 2.

Example H

A hydrothermal process was used to synthesize a ZSM-5 molecular sieve (marked as Z5 (50)-700 nm) with a Si/Al molar ratio of 50 and an average particle size of 700 nm, comprising the steps of:

0.41 g of aluminum isopropoxide was added to a mixed solution of 24.67 g of tetrapropylammonium hydroxide solution (25 wt %) and 17.89 g of deionized water. The mixture was placed and stirred at room temperature for 12 h, then 21.06 g of ethyl orthosilicate was added dropwise. After stirring for 12 h, 15.18 g urea was added to the mixed system and stirring was continued for 1 h. The mother liquor was transferred to a PTFE lined autoclave and hydrothermally treated in a 180° C. oven for 48 h. The liquor was centrifugally separated and repeatedly washed with deionized water until the supernatant was neutral, and dried to obtain a solid product, namely an uncalcined ZSM-5 sample, wherein an XRD spectrum thereof was shown in FIG. 2.

Example i

A hydrothermal process was used to synthesize a ZSM-5 molecular sieve (marked as Z5 (50)-700 nm) with a Si/Al molar ratio of 50 and an average particle size of 700 nm, comprising the steps of:

0.41 g of aluminum isopropoxide was added to a mixed solution of 24.67 g of tetrapropylammonium hydroxide solution (25 wt %) and 17.89 g of deionized water. The mixture was placed and stirred at room temperature for 12 h, then 21.06 g of ethyl orthosilicate was added dropwise. After stirring for 12 h, 24.30 g ammonium carbonate was added to the mixed system and stirring was continued for 1 h. The mother liquor was transferred to a PTFE lined autoclave and hydrothermally treated in a 180° C. oven for 48 h. The liquor was centrifugally separated and repeatedly washed with deionized water until the supernatant was neutral, and dried to obtain a solid product, namely an uncalcined ZSM-5 sample, wherein an XRD spectrum thereof was shown in FIG. 2.

Example J

A hydrothermal process was used to synthesize a ZSM-5 molecular sieve (marked as Z5 (50)-700 nm) with a Si/Al molar ratio of 50 and an average particle size of 700 nm, comprising the steps of:

0.41 g of aluminum isopropoxide was added to a mixed solution of 39.96 g of tetrapropylammonium hydroxide solution (25 wt %) and 17.89 g of deionized water. The mixture was placed and stirred at room temperature for 12 h, then 21.06 g of ethyl orthosilicate was added dropwise. After stirring for 12 h, 27.99 g ammonium bicarbonate was added to the mixed system and stirring was continued for 1 h. The mother liquor was transferred to a PTFE lined autoclave and hydrothermally treated in a 180° C. oven for 48 h. The liquor was centrifugally separated and repeatedly washed with deionized water until the supernatant was neutral, and dried to obtain a solid product, namely an uncalcined ZSM-5 sample, wherein an XRD spectrum thereof was shown in FIG. 2.

Example 1

10 g of MnO prepared in Example a, 10 g of Z5(50)-450 nm prepared in Example b and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-1.

Example 2

10 g of $Cr_2O_3$ prepared in Example c, 10 g of Z5(50)-450 nm prepared in Example b and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-2.

Example 3

10 g of $CrMnO_x$ prepared in Example d, 10 g of Z5(50)-450 nm prepared in Example b and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-3.

Example 4

10 g of $Cr_2O_3$ prepared in Example c, 10 g of Z11(50)-450 nm prepared in Example e and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-4.

Example 5

10 g of $Cr_2O_3$ prepared in Example c, 10 g of Z5(50)-200 nm prepared in Example f and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-5.

Example 6

10 g of $Cr_2O_3$ prepared in Example c, 10 g of Z5(50)-300 nm prepared in Example g and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-6.

Example 7

10 g of $Cr_2O_3$ prepared in Example c, 10 g of Z5(50)-700 nm prepared in Example h and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-7. For the catalyst SSL-7, the XRD spectrum was shown in FIG. 1, the SEM photograph was shown in FIG. 3, and the scanning photograph was shown in FIG. 4.

Example 8

10 g of $Cr_2O_3$ prepared in Example c, 10 g of Z5(50)-700 nm prepared in Example h and, and a mixture of silica sol and aluminum nitrate (with an equivalent total weight of $SiO_2$ and $Al_2O_3$ of 4 g, a Si/Al ratio of 100) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-8.

Example 9

20 g of $Cr_2O_3$ prepared in Example c, 10 g of Z5(50)-700 nm prepared in Example h and 10 g of silica sol (with 4 g of $SiO_2$ contained) were mechanically mixed, extruded into a strip shape, and crystallized in tetrapropylammonium hydroxide vapor at 170° C. for 48 hours. The crystallized catalyst was calcined at 550° C. for 5 hours to obtain catalyst SSL-9.

Example 10

10 g of $Cr_2O_3$ prepared in Example c, 10 g of Z5(50)-700 nm prepared in Example i and 10 g of silica sol (with 4 g of $SiO_2$ contained) were mechanically mixed, extruded into a strip shape, and crystallized in tetrabutylammonium hydroxide vapor at 170° C. for 48 hours. The crystallized catalyst was calcined at 550° C. for 5 hours to obtain catalyst SSL-10.

Example 11

10 g of $Cr_2O_3$ prepared in Example c, 10 g of Z5(50)-700 nm prepared in Example j and 10 g of silica sol (with 4 g of $SiO_2$ contained) were mechanically mixed, extruded into a strip shape, and crystallized in ammonia vapor at 170° C. for 72 hours. The crystallized catalyst was calcined at 550° C. for 5 hours to obtain catalyst SSL-11.

Comparative Example 1

10 g of $Cr_2O_3$ prepared in Example c, 10 g of Z5(50)-700 nm prepared in Example h were mechanically mixed. The XRD spectrum of the catalyst was shown in FIG. 1. Catalyst particles of 20-40 mesh were obtained from granulating and crushing.

Comparative Example 2

10 g of $Cr_2O_3$ prepared in Example c, 10 g of Z5(50)-700 nm prepared in Example h and 10 g of silica sol (with 4 g of $SiO_2$ contained) were mechanically mixed, and extruded into a strip shape, to obtain catalysts. XRD spectrum and SEM photograph of the catalysts were shown in FIGS. 1 and 3, respectively, from which the presence of amorphous silica was observed. A scanning photograph of the catalysts was shown in FIG. 5.

Comparative Example 3

10 g of $Cr_2O_3$ prepared in Example c, 10 g of Z5(50)-700 nm prepared in Example h and 10 g of silica sol (with 4 g of $SiO_2$ contained) were mechanically mixed, extruded into a strip shape, and crystallized in water vapour at 170° C. for 48 hours. The crystallized catalyst was calcined at 550° C. for 5 hours to obtain catalysts.

Characterization Example

Figure 2:
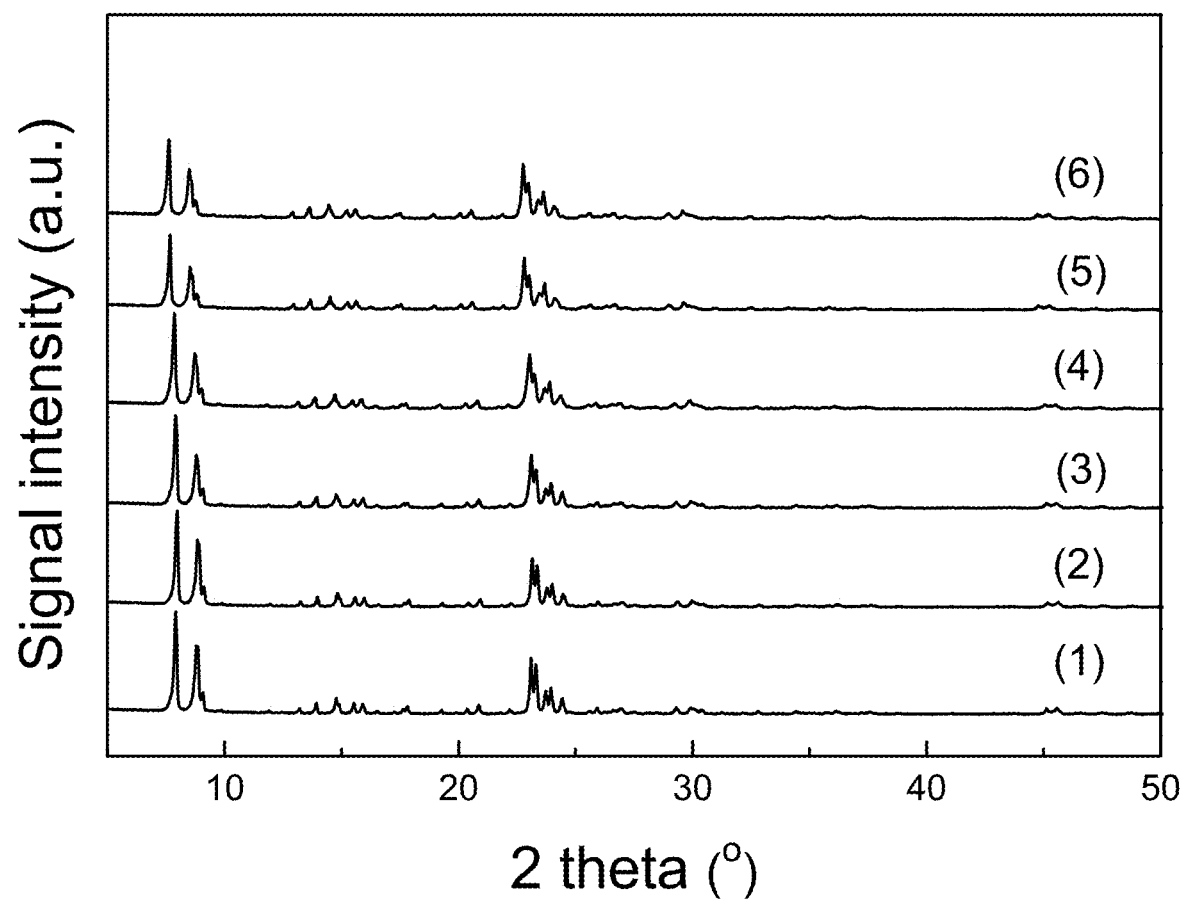
In FIG. 2, panels (1), (2), (3), (4), (5) and (6) are XRD spectra of the molecular sieves in Examples b, f, g, h, i and j, respectively.
Figure 3:
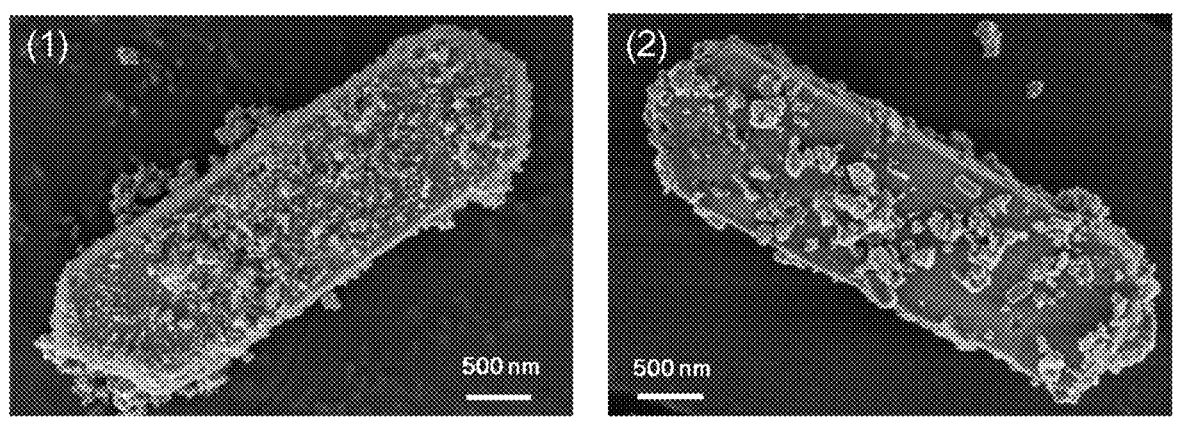
In FIG. 3, panels (1) and (2) are SEM images of the catalysts obtained in Comparative Example 2 and Example 7, respectively.
Figure 4:
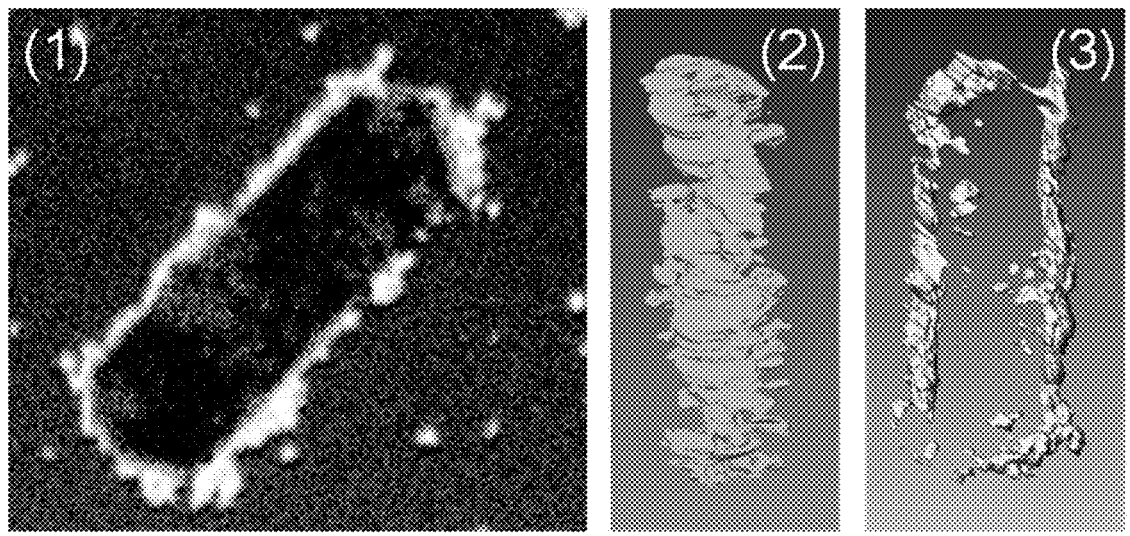
In FIG. 4, panels (1), (2) and (3) are respectively scanning photographs of the catalyst obtained in Example 7, and a nano-CT photographs of crystal planes (100) and (010) of the ZSM-5 molecular sieve.

The catalysts of some of the Examples according to the present invention and Comparative Examples were characterized and the results were illustrated below referring to FIGS. 1-5:

The XRD spectra of the catalyst SSL-7, the catalyst obtained in the Comparative Example 2 and the catalyst obtained in the Comparative Example 1 were respectively shown as panels (1), (2) and (3) in FIG. 1, and all had obvious ZSM-5 characteristic peaks, wherein the XRD spectrum of the catalyst SSL-7 did not substantially comprise a characteristic diffraction peak of amorphous silica, while a characteristic diffraction peak of the amorphous silica could be obviously seen from the XRD spectrum of the catalyst obtained in the Comparative Example 2. Furthermore, the characteristic peak intensity of ZSM-5 of the catalyst SSL-7 was higher than that of the catalyst obtained in the Comparative Example 2 and the catalyst obtained in the Comparative Example 1;

The XRD spectra of the molecular sieves obtained in the Examples b, f, g, h, i and j were respectively shown in panels (1), (2), (3), (4), (5) and (6) in FIG. 2, and all had obvious ZSM-5 characteristic peaks;

The SEM images of the catalyst of Comparative Example 2 and catalyst SSL-7 were shown in panels (1) and (2) of FIG. 3, respectively, and it could be seen from FIG. 3 that the catalyst of Comparative Example 2 had oxide grains and smaller binder particles dispersed on the surface of the molecular sieve grains, while the binder particles disappeared on the surface of the molecular sieve in catalyst SSL-7 but molecular sieves were formed;

A scanning photograph of catalyst SSL-7 was shown in FIG. 4, panel (1), wherein about 75% of the oxide was distributed on the surface of the molecular sieve. Less than 25% of the oxide was distributed in a range having a distance of more than 100 nm from the surface of the molecular sieve crystal grains. The nano-CT photographs of the crystal planes (100) and (010) of the molecular sieve were shown in panels (2) and (3) in FIG. 4, respectively. As could be seen from FIG. 4, panel (2), the oxide was selectively distributed mainly on the crystal plane (100) and the adjacent crystal plane (101) of the molecular sieve, while as could be seen from FIG. 4, panel (3), the distribution on the crystal plane (010) was less. Specifically, about 80% of the oxide was distributed on the crystal planes (100) and (101), and about 20% was distributed on the crystal plane (010). Accounting the weight of the metal oxide distributed in unit area on the crystal plane (010) of the molecular sieve as 1, the weight of the metal oxide distributed in unit area on the crystal plane (101) was more than 3.

Figure 5:
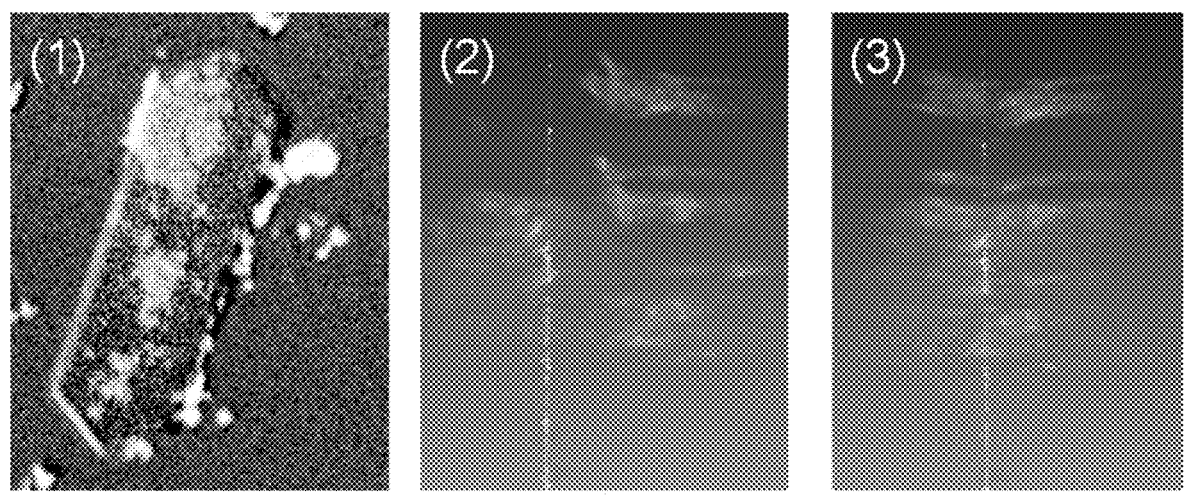
In FIG. 5, panels (1), (2) and (3) are respectively scanning photographs of the catalyst obtained in Comparative Example 2, and nano-CT photographs of crystal planes (100) and (010) of the ZSM-5 molecular sieve.

The scanning photograph of the catalyst of Comparative Example 2 was shown in FIG. 5, panel (1), wherein the nano-CT photographs of crystal plane (100) and crystal plane (010) were respectively shown in FIG. 5, panels (2) and (3), and the distribution of the metal oxide on the surface of the molecular sieve did not show any selectivity, without the characteristics of distribution on any specific crystal plane.

EVALUATION A OF CATALYST PERFORMANCE

The catalysts of Examples 1 to 11 and Comparative Examples 1 to 3 were used to evaluate the performance thereof by taking 1.5 g of each catalyst. The catalyst was evaluated as follows: respectively weighing 1.5 g of the SSL 1-SSL 11 catalysts prepared in the Examples 1-11 or 1.5 g of the catalysts prepared in the Comparative Examples 1-3, crushing the catalysts to 20-40 meshes, and filling the crushed catalysts into a reactor. The catalyst evaluation was carried out at a reaction temperature of 395° C., a pressure of 6.0 MPa, a feed gas $H_2$/CO ratio of 1.0 and a volume space velocity of 2000 h$^{-1}$. The catalyst was pretreated with H$_2$ at 395° C. for 2 h before reaction. The raw material gases H$_2$/CO/N$_2$, and product were analyzed on line by gas chromatography, wherein the quantitative analysis of the products was realized by taking N$_2$ as an internal standard. The products were separated by using three columns, wherein one column was a hayesep-Q packed column, where the separated products were introduced into a thermal conductivity cell detector for detecting hydrogen, nitrogen, carbon monoxide, carbon dioxide, methane and the like. Aliphatic hydrocarbons and aromatic hydrocarbons were cut by using the dean switch technology of Agilent, and detected respectively by two sets of hydrogen flame detectors, wherein one column was an HP-PLOT Al$_2$N$_3$ capillary column, and the products were fed to the hydrogen flame detectors to detect aliphatic hydrocarbon products such as methane, ethane, ethylene, propane, propylene, butane, butylene and the like; and the other column was a DB-WAXetr capillary column, and the products were fed to a hydrogen flame detector to detect aromatic hydrocarbon products such as benzene, toluene, xylene, C$_{9+}$ aromatic hydrocarbons and the like. The results of CO conversion, selectivity to aromatics, and selectivity to C$_6$-C$_8$ aromatics were shown in Table 1.

EVALUATION B OF CATALYST PERFORMANCE 1.5 g of the catalyst of Example 7 was used for performance evaluation. The catalyst evaluation process was as follows: 1.5 g of SSL7 catalyst prepared in Example 7 was weighed, crushed to 20-40 mesh and loaded into a reactor. Different reaction temperatures, pressures, feed gas compositions and volume space velocities were set, and catalyst evaluation was carried out under different conditions. The catalyst was pretreated with H$_2$ at 395° C. for 2 h before reaction. The reaction conditions and the evaluation results (CO conversion, selectivity to aromatics, and selectivity to C$_6$-C$_5$ aromatics) were shown in Table 2.

TABLE 1

| Catalyst | Metal Oxide | Molecular sieves (Si/Al ratio) and particle size | Binder | Weight ratio of metal oxide:molecular sieve:binder | Crystallization method | CO Conversion (%) | Selectivity to aromatics (%) | Selectivity to C$_6$-C$_8$ aromatics (%) |
|---|---|---|---|---|---|---|---|---|
| SSL1 | MnO | Z5(50) 450 nm | Silica sol | 1:1:0.4 | TPAOH, 170° C., 48 h | 45 | 71 | 58 |
| SSL2 | Cr$_2$O$_3$ | Z5(50) 450 nm | Silica sol | 1:1:0.4 | TPAOH, 170° C., 48 h | 42 | 75 | 54 |
| SSL3 | CrMnO$_x$ | Z5(100) 450 nm | Silica sol | 1:1:0.4 | TPAOH, 170° C., 48 h | 40 | 74 | 56 |
| SSL4 | Cr$_2$O$_3$ | Z11(50) 450 nm | Silica sol | 1:1:0.4 | TPAOH, 170° C., 48 h | 40 | 70 | 51 |
| SSL5 | Cr$_2$O$_3$ | Z5(50) 200 nm | Silica sol | 1:1:0.4 | TPAOH, 170° C., 48 h | 45 | 73 | 24 |
| SSL6 | Cr$_2$O$_3$ | Z5(50) 300 nm | Silica sol | 1:1:0.4 | TPAOH, 170° C., 48 h | 43 | 73 | 35 |
| SSL7 | Cr$_2$O$_3$ | Z5(50) 700 nm | Silica sol | 1:1:0.4 | TPAOH, 170° C., 48 h | 41 | 74 | 58 |
| SSL8 | Cr$_2$O$_3$ | Z5(50) 700 nm | Silica sol + aluminum nitrate (100:1) | 1:1:0.4 | TPAOH, 170° C., 48 h | 44 | 75 | 53 |
| SSL9 | Cr$_2$O$_3$ | Z5(50) 700 nm | Silica sol | 2:1:0.4 | TPAOH, 170° C., 48 h | 38 | 72 | 57 |
| SSL10 | Cr$_2$O$_3$ | Z5(50) 700 nm | Silica sol | 1:1:0.4 | TBAOH, 170° C., 48 h | 40 | 76 | 56 |
| SSL11 | Cr$_2$O$_3$ | Z5(50) 700 nm | Silica sol | 1:1:0.4 | NH$_3$·H$_2$O, 170° C., 72 h | 33 | 73 | 53 |
| Comparative example 1 | Cr$_2$O$_3$ | Z5(50) 700 nm | / | 1:1 | / | 23 | 81 | 46 |
| Comparative example 2 | Cr$_2$O$_3$ | Z5(50) 700 nm | Silica sol | 1:1:0.4 | / | 18 | 75 | 52 |
| Comparative example 3 | Cr$_2$O$_3$ | Z5(50) 700 nm | Silica sol | 1:1:0.4 | H$_2$O, 170° C., 48 h | 31 | 72 | 49 |

TABLE 2

| H$_2$/CO (mol/mol) | Temperature (° C.) | Pressure (MPa) | Space velocity (h$^{-1}$) | CO Conversion (mol %) | Selectivity to aromatics (mol %) | Selectivity to C$_6$-C$_8$ aromatics (mol %) |
|---|---|---|---|---|---|---|
| 1.0 | 350 | 8.0 | 8000 | 43 | 73 | 52 |
| 0.5 | 395 | 8.0 | 10000 | 38 | 75 | 53 |
| 4.0 | 350 | 5.0 | 15000 | 36 | 70 | 58 |
| 1.0 | 395 | 5.0 | 15000 | 37 | 79 | 57 |
| 1.0 | 450 | 5.0 | 15000 | 42 | 71 | 60 |
| 0.5 | 395 | 4.0 | 5000 | 40 | 76 | 54 |

The preferred embodiments of the present invention have been described above in detail, but the present invention is not limited thereto. Within the scope of the technical idea of the invention, many simple modifications can be made to the technical solution of the invention, including various technical features being combined in any other suitable way, and these simple modifications and combinations should also be regarded as the disclosure of the invention, and all fall within the scope of the invention.

The invention claimed is:

1. A catalyst comprising a metal oxide and a molecular sieve having a topological pore structure in a crystal form, the metal oxide being concentrated on the surface of the molecular sieve , wherein the crystal grains of the molecular sieve expose at least three families of crystal planes, and no more than 30% of the meta oxide is distributed on the family of crystal plane having relatively the largest channel size in topology among the three families of crystal planes.

2. The catalyst according to claim 1, wherein at least 70% of the metal oxide is distributed on the two families of crystal planes having the topologically relatively smallest channel size; or
taking a weight of metal oxide distributed per area on the crystal plane with the topologically largest channel size as 1, then the weight of metal oxide distributed per area on the crystal plane with the topologically smallest channel size is greater than 2.

3. The catalyst according to claim 1, wherein at least 50% of the metal oxide is distributed on the surface of the molecular sieve.

4. The catalyst according to claim 1, wherein at most 30% of the metal oxide is distributed beyond a distance of more than 200 nm from the surface of the molecular sieve crystal grains.

5. The catalyst according to claim 1, wherein the molecular sieve is selected from the group consisting of MFI, MEL, AEL, and TON; and/or
the metal component of the metal oxide is selected from the group consisting of rare earth metals, Group IVB, Group VIIB, Group VIII, Group IB, Group IIB, and Group IIIA elements; and/or
in the catalyst, the weight ratio of the metal oxide to the molecular sieve is (0.2-5.0): 1.

6. The catalyst according to claim 1, wherein the XRD spectrum of the catalyst is substantially free of characteristic diffraction peaks of amorphous silica and/or amorphous alumina.

7. The catalyst according to claim 1, wherein the catalyst particles have a particle size of from 0.1 mm to 10.0 mm.

8. The catalyst according to claim 1, wherein the molecular sieve is a ZSM-5 molecular sieve; and at least 70% of the metal oxide is distributed on the crystal plane (100) and the crystal plane (101) of the ZSM-5 molecular sieve;
or, the molecular sieve is a ZSM-11 molecular sieve, and at least 50% of the metal oxide is distributed on the crystal plane (101) of the ZSM-11 molecular sieve.

9. A process for preparing the catalyst according to claim 1, comprising: mixing and shaping a metal oxide, a molecular sieve in the prepared form and a binder, carrying out a second crystallization treatment in a second template agent vapor atmosphere, and calcining to obtain the catalyst, wherein the molecular sieve in the prepared form is prepared with the aid of a first templating agent that is the same as or different from the second templating agent without calcination.

10. The process according to claim 9, wherein the preparation of the molecular sieve comprises preparing a crystallization mother liquor, and adding an ammonium based adjuvant during the preparation process of the mother liquor.

11. The process according to claim 10, wherein the ammonium based adjuvant is a substance capable of providing ammonium ions;
wherein the molar ratio of the ammonium based adjuvant to the silicon source calculated as SiO2 in the molecular sieve is 0.2-5.0.

12. The process according to claim 9, wherein the second template is selected from aqueous ammonia, triethylamine, tetraethylammonium bromide, tetraethylammonium hydroxide, tetrapropylammonium bromide, tetrapropylammonium hydroxide, tetrabutylammonium bromide, and tetrabutylammonium hydroxide;
and/or the second crystallization is carried out at a crystallization temperature of 100-180° C. for a crystallization duration of 12-100 hours;
and/or, the calcination is carried out under conditions at a calcining temperature of 500-700° C. for a calcining duration of 2-10 hours.

13. The process according to claim 9, wherein the weight ratio of the metal oxide/molecular sieve/binder is (0.2-5.0): 1: (0.2- 0.6).

14. A process for producing aromatic hydrocarbons and/or light hydrocarbons by conversion of synthesis gas, comprising contacting and reacting a synthesis gas as raw material with the catalyst according to claim 1 to obtain a stream comprising aromatic hydrocarbons and/or light hydrocarbons.

15. The catalyst according to claim 1, wherein, taking the weight of metal oxide distributed per area on the one family of crystal plane having the topologically largest channel size as 1, the weight of metal oxide distributed per area on the other two families of crystal planes with the topologically smallest channel size is greater than 3.

16. The catalyst according to claim 1, wherein at most 25% of the metal oxide is distributed at a distance of more than 100 nm from the surface of the molecular sieve crystal grains.

17. The process according to claim 11, wherein the ammonium based adjuvant is selected from ammonia, urea, ammonium carbonate and ammonium bicarbonate.

* * * * *